(12) United States Patent
Ebisawa

(10) Patent No.: US 7,766,479 B2
(45) Date of Patent: Aug. 3, 2010

(54) VIEW POINT DETECTING DEVICE

(75) Inventor: Yoshinobu Ebisawa, Hamamatsu (JP)

(73) Assignee: National University Corporation Shizuoka University (JP)

( * ) Notice: Subject to any disclaimer, the term of this patent is extended or adjusted under 35 U.S.C. 154(b) by 0 days.

(21) Appl. No.: 12/295,502

(22) PCT Filed: Mar. 7, 2007

(86) PCT No.: PCT/JP2007/054434
§ 371 (c)(1),
(2), (4) Date: Apr. 15, 2009

(87) PCT Pub. No.: WO2007/113975
PCT Pub. Date: Oct. 11, 2007

(65) Prior Publication Data
US 2009/0219484 A1 Sep. 3, 2009

(30) Foreign Application Priority Data
Mar. 31, 2006 (JP) .............................. 2006-100205

(51) Int. Cl.
A61B 3/14 (2006.01)
(52) U.S. Cl. ........................ 351/209; 351/210; 351/214; 351/216
(58) Field of Classification Search ................. 351/205, 351/209, 210, 211, 214, 216, 221
See application file for complete search history.

(56) References Cited

U.S. PATENT DOCUMENTS

| 4,993,825 | A | * | 2/1991 | Abe et al. | 351/210 |
| 5,886,768 | A | * | 3/1999 | Knopp et al. | 351/212 |
| 6,588,902 | B2 | | 7/2003 | Isogai | |
| 2005/0195277 | A1 | | 9/2005 | Yamasaki | |

FOREIGN PATENT DOCUMENTS

JP 10-108840 4/1998

(Continued)

OTHER PUBLICATIONS

International Search Report issued Jun. 19, 2007.

(Continued)

Primary Examiner—Huy K Mai
(74) Attorney, Agent, or Firm—Ostrolenk Faber LLP

(57) ABSTRACT

A gaze point detecting device 1 detects a gaze point of an object person by projecting a display image displayed by an LCD 8 to outside via a finder 4 and capturing an eye image of the object person by a CCD 11 in response to illumination light irradiated toward outside from the finder 4, and the device comprises an optical system 5 arranged spaced only a focal length apart from a display surface 8a on an optical path of an image displaying optical system between the LCD 8 and the finder 4; the optical system 5 being arranged on an optical path of an imaging optical system between the finder 4 and the CCD 11; a telecentric optical system including a diaphragm 9 arranged spaced only a focal length apart from the optical system 5 on the optical path; and a controller 3 that detects a position of the gaze point of the object person based on the eye image captured by the CCD 11.

7 Claims, 16 Drawing Sheets

FOREIGN PATENT DOCUMENTS

| | | |
|---|---|---|
| JP | 10-307314 | 11/1998 |
| JP | 2000-10723 | 1/2000 |
| JP | 2000-210257 | 8/2000 |
| JP | 2001-134371 | 5/2001 |
| JP | 2005-125086 | 5/2005 |
| JP | 2005-182247 | 7/2005 |
| JP | 2005-252732 | 9/2005 |
| JP | 2005-279305 | 10/2005 |
| JP | 2005-286141 | 10/2005 |

OTHER PUBLICATIONS

Talmi et al., "Eye and gaze tracking for visually controlled interactive stereoscopic displays," Signal Processing: *Image Communication* 14 (1999) p. 799-810.

* cited by examiner

Fig.4
(a)
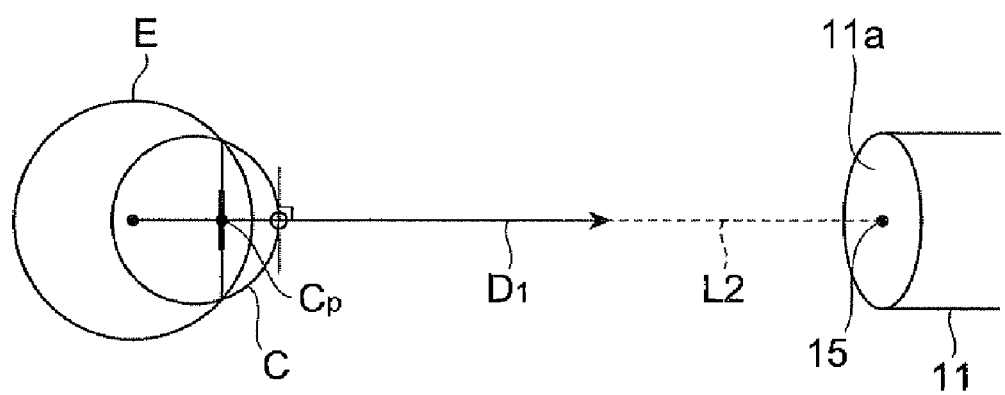
(b)
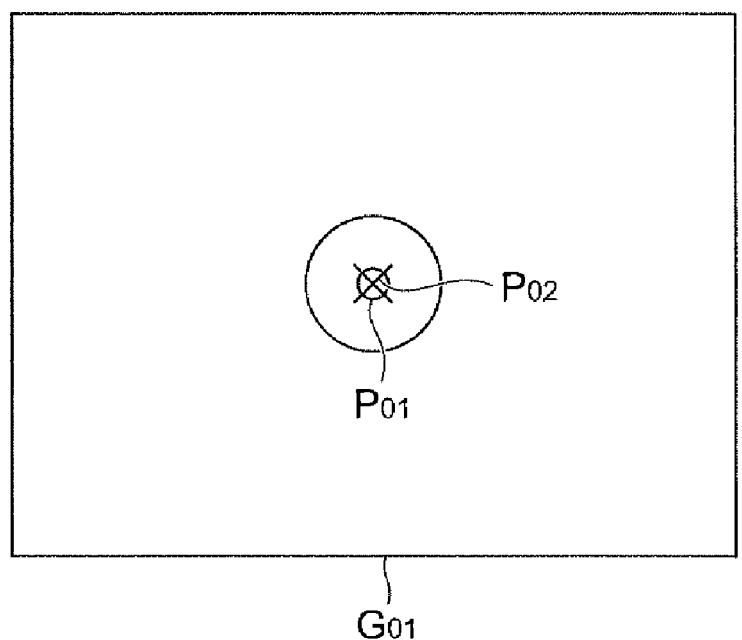

Fig.5
(a)
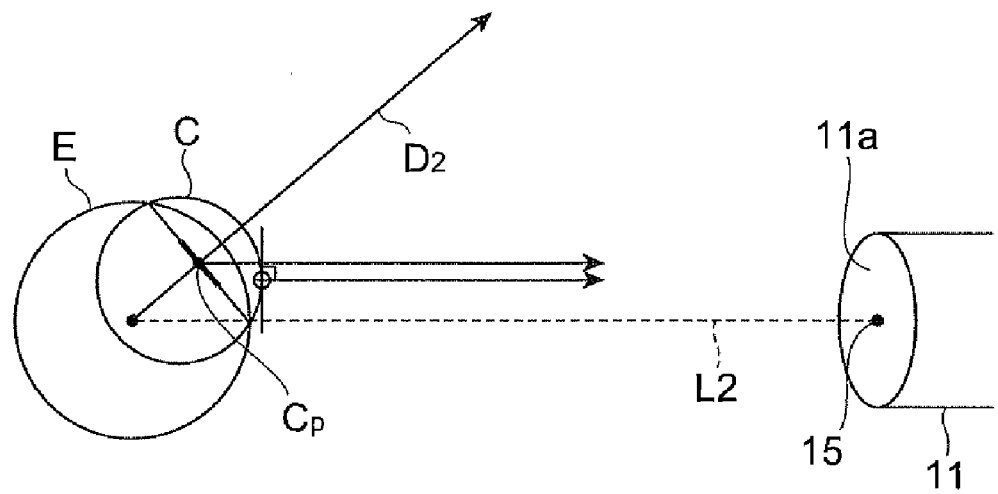
(b)
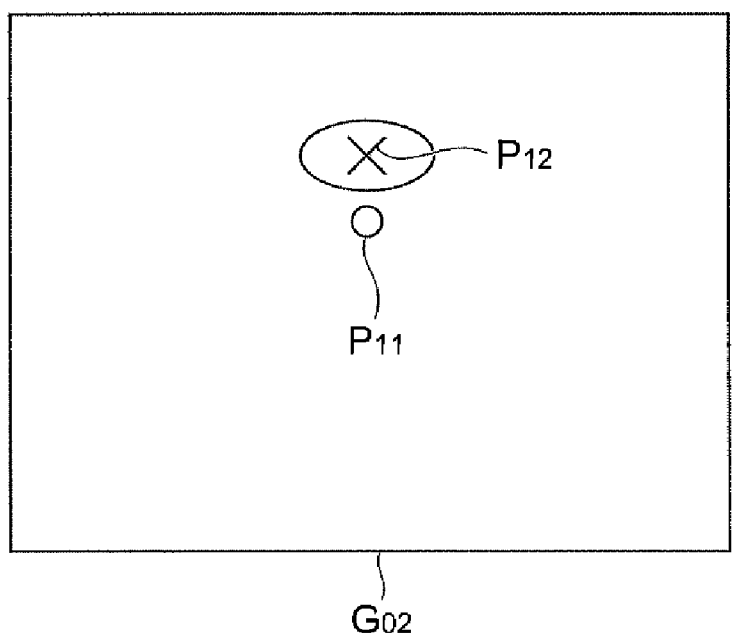

Fig.9
(a)
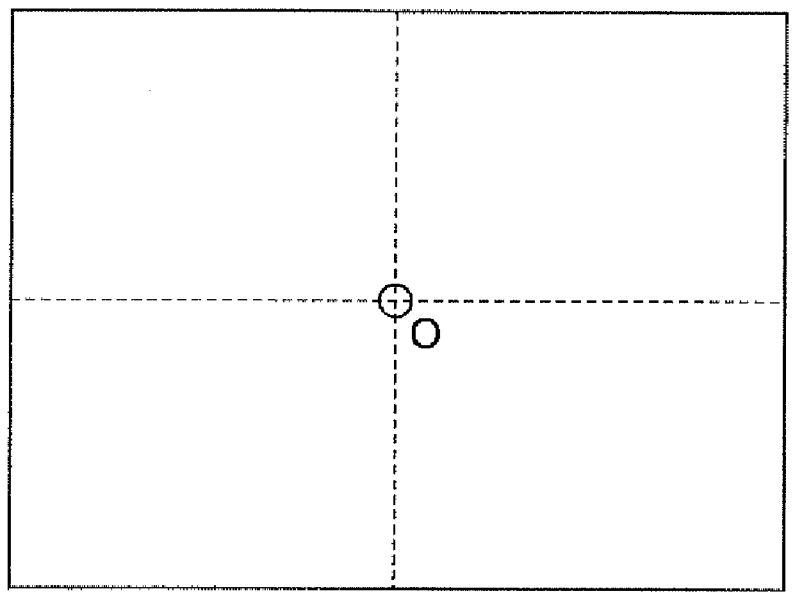
(b)
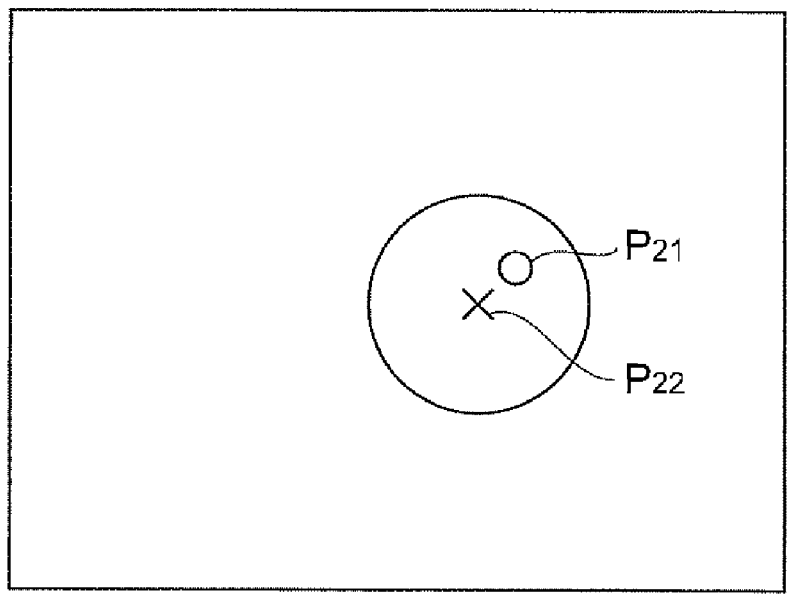

Fig.10
(a)
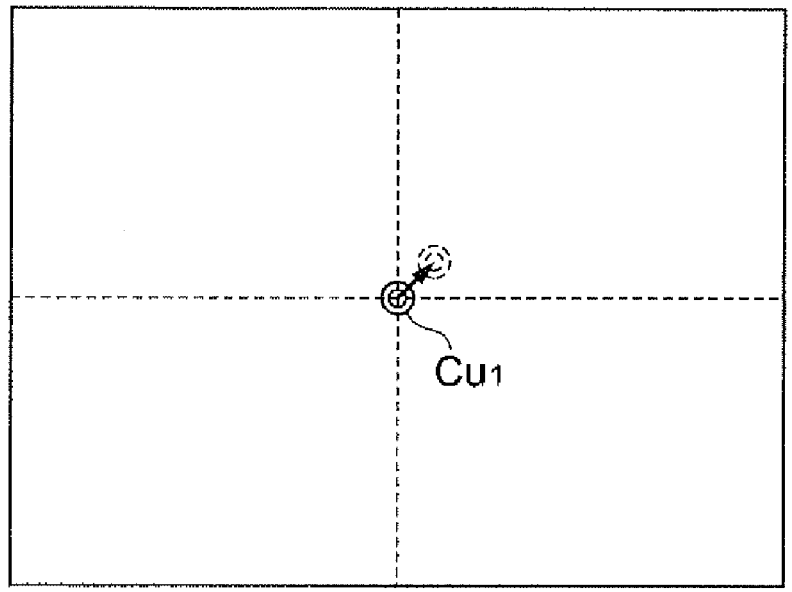
(b)
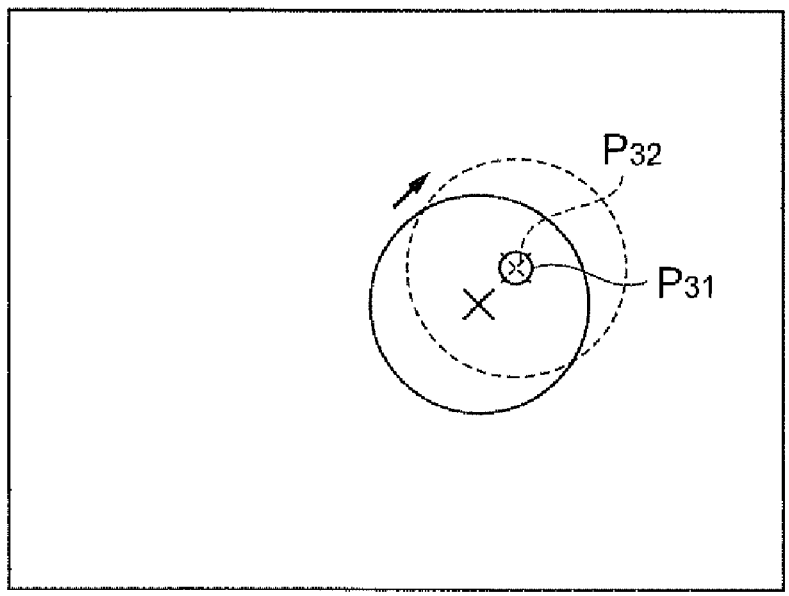

Fig.11
(a)
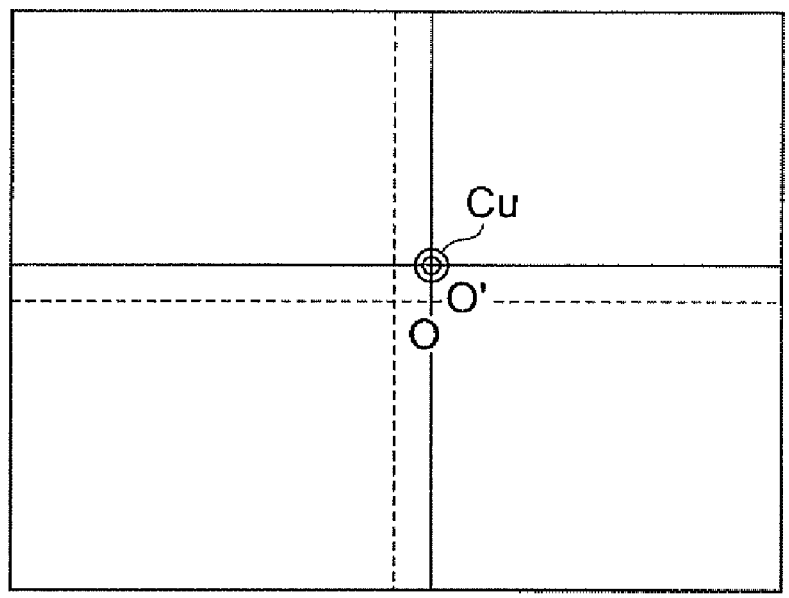
(b)
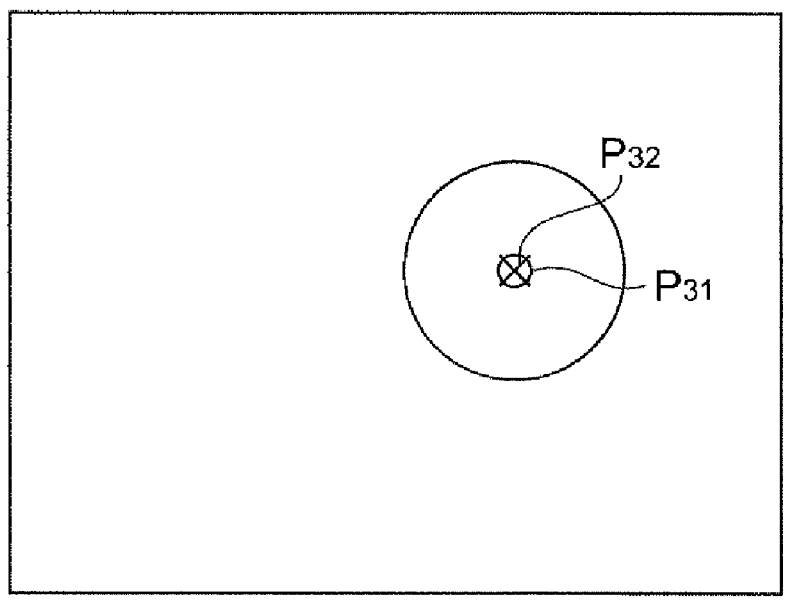

Fig.12
(a)
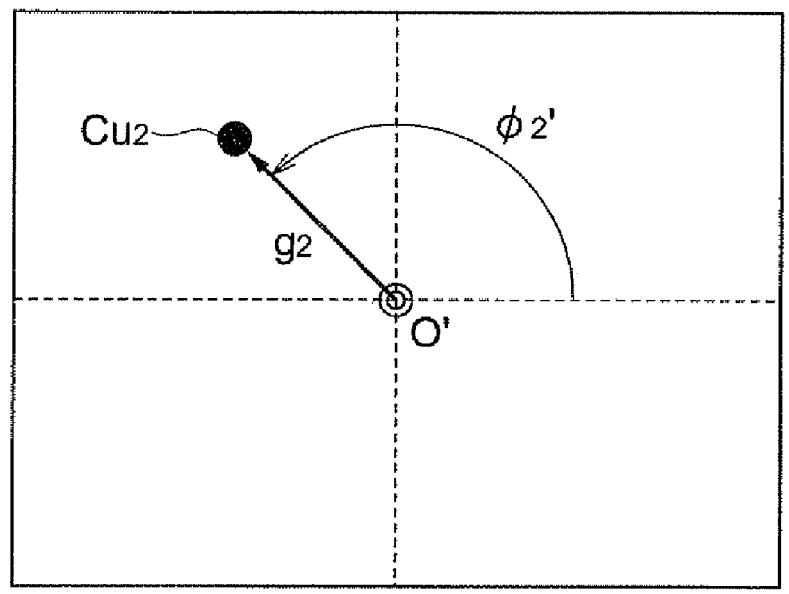
(b)
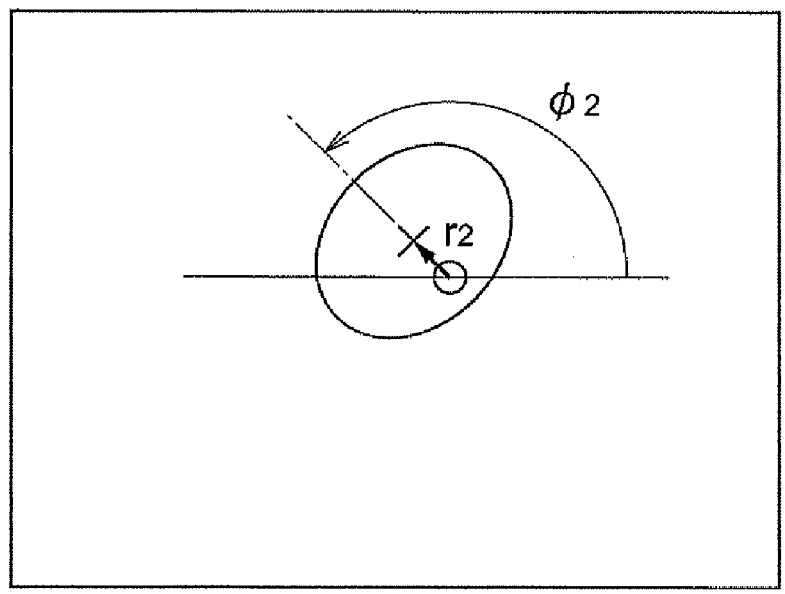

*Fig.15*
(a)
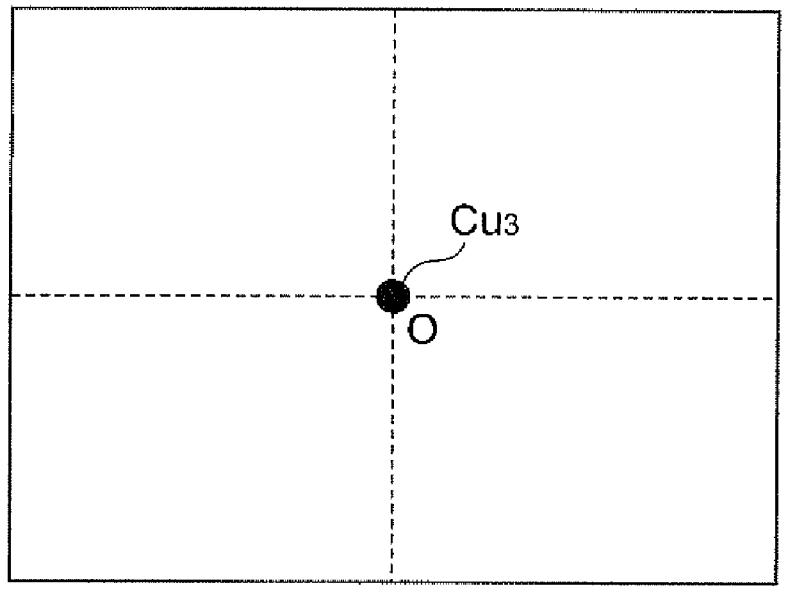
(b)
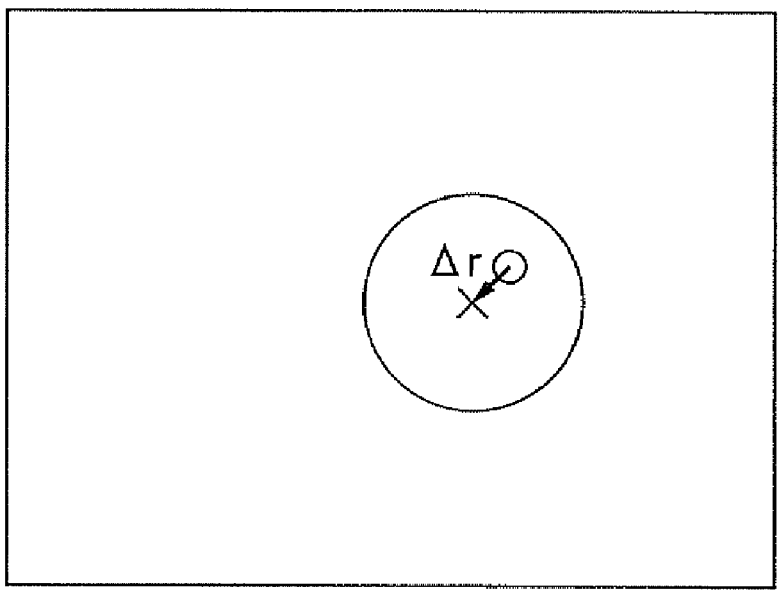

Fig.16
(a)
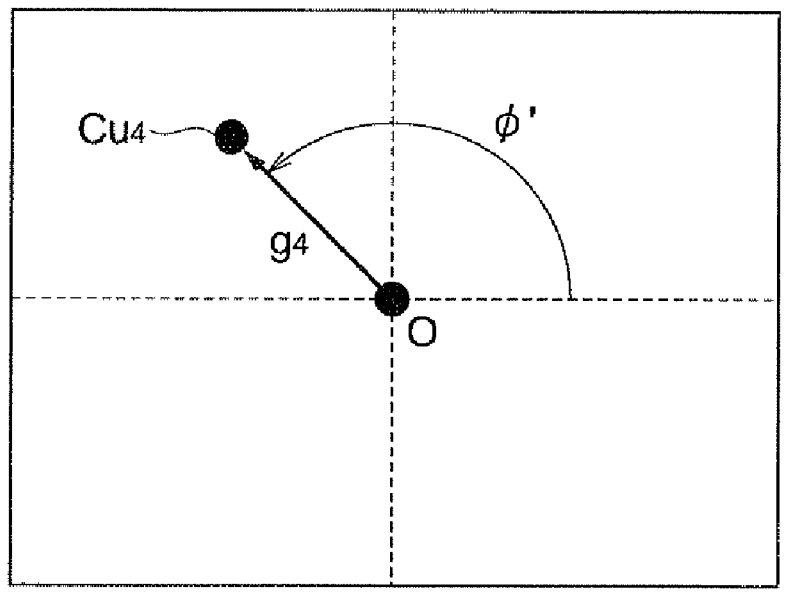
(b)
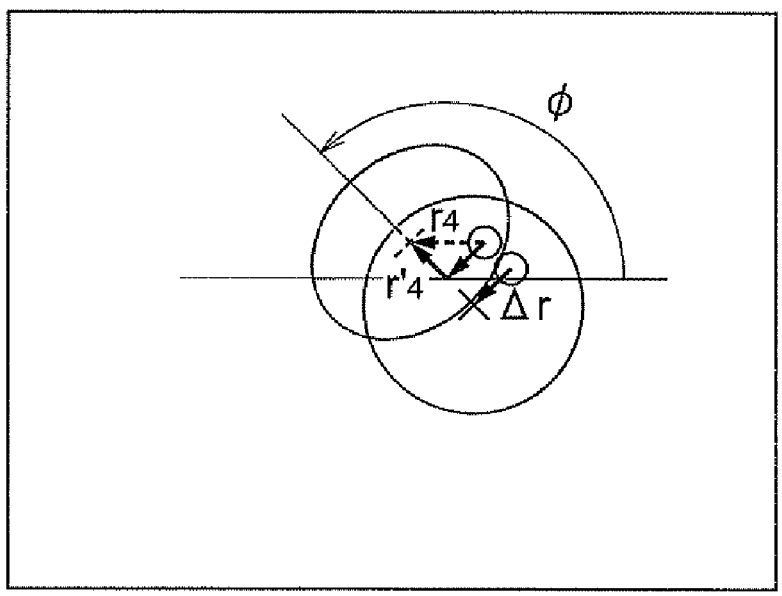

VIEW POINT DETECTING DEVICE

CROSS-REFERENCE TO RELATED APPLICATION

The present application is a 35 U.S.C. §371 national phase conversion of PCT/JP2007/054434 filed Mar. 7, 2007 and claims priority of JP2006-100205 filed Mar. 31, 2006, both incorporated herein in their entirety.

TECHNICAL FIELD

The present invention relates to a line of sight detecting device that detects a gaze point of an object person to an image displayed.

BACKGROUND ART

There has been conventionally known a device that detects a line of sight direction or a gaze point of an object person on an object to be observed, such as a display. For example, in a non-patent document 1 described below, there is described a device that measures which portion in a display screen an object person gazes at by placing a camera at a distance 50 to 80 cm from a face of the object person. Also, there is known a pointing device that detects a pupil from a face image using a camera and moves a cursor on a display screen in response to a movement of the pupil caused by a movement of the head of the object person (refer to the patent document 1 below).

On another front, a head mount display type line of sight detecting device (hereinafter, called HMD) capable of responding to large movements of a head of an object person is expected in various applications. For example, there is disclosed an HMD-type line of sight detecting device which includes a camera that displays an image output from a personal computer and detects a gaze point on the image, and which finds an error caused by a movement of a head of an object person and corrects positional deviation of the detection result based on the error (refer to patent document 2 below). There is also disclosed an HMD-type line of sight detecting device that calculates which portion of an object to be observed in outside is gazed at carefully by detecting a line of sight direction of the object person (refer to patent document 3 below).

[Patent Document 1] Japanese Unexamined Patent Application No. 2005-182247
[Patent Document 2] Japanese Unexamined Patent Application No. 2001-134371
[Patent Document 3] Japanese Unexamined Patent Application No. 2005-286141
[Non-patent Document 1] Kay Talmi, Jin Liu "Eye and gaze tracking for visually controlled interactive stereoscopic displays", Signal Processing Image Communication vol. 14, August 1999, p. 799-810

DISCLOSURE OF THE INVENTION

However, it is difficult for the conventional line of sight detecting devices described above to precisely detect a line of sight or a gaze point to an object to be observed, such as a display, when the position of an object person relative to the device changes due to a deviation of a mounting position. This is because the way how the object to be observed appears to the object person and the position of a face image of the object person change as the position of the head of the object person changes. The line of sight detecting device described in patent document 2 above has a function of recalibrating when a line of sight input becomes difficult. However, frequent calibrating operations due to mounting deviations reduce the convenience for a user.

Then, the present invention is made in consideration of such problems and intends to provide a gaze point detecting device capable of improving precision in gaze point detection of an object person to a display image while maintaining the convenience for a user.

MEANS FOR SOLVING THE PROBLEM

In order to solve the problems above, a gaze point detecting device of the present invention is the one for detecting a gaze point in a display image of an object person by projecting the display image displayed by an image displaying means to outside via a window and capturing an eye image of the object person through an imaging means, in response to an illumination light irradiated toward the object person positioned outside of the window, the device comprising: a telecentric lens arranged on an optical path between the window and the imaging means; a lens arranged on an optical path between the image displaying means and the window, for constituting a part of the telecentric lens; and a detecting means for detecting a position of gaze point of the object person based on the eye image captured by the imaging means.

According to such a gaze point detecting device, when a display image is projected from the window to outside, it passes the telecentric lens from a display surface, thereby one point on a display surface and an angle of the line of sight of the object person correspond on a one-to-one basis, and at the same time the eye image of the object person is displayed on the imaging means through the telecentric lens in response to irradiation of the illumination light. Therefore, a size of the captured eye image does not change even if the position of the object person changes in the front/back direction relative to the window. With this arrangement, when the position of gaze point is detected based on the eye image of object person, an actual gaze point of the object person on the display surface and the line of sight direction detected correspond on a one-to-one basis. Thus, an error in the gaze point detection of the object person is reduced even if the position of the object person relative to the window changes.

EFFECTS OF THE INVENTION

According to a gaze point detecting device of the present invention, it is possible to improve the precision in detection of the gaze point of the object person to a display image while maintaining convenience for a user.

BRIEF DESCRIPTION OF THE DRAWINGS

FIGS. 4(a) and 4(b) are views illustrating a principle of a gaze point detecting process by a controller in FIG. 1, and FIG. 4(a) is a view illustrating a positional relationship between an eye ball of an object person and an imaging surface, and FIG. 4(b) is a view illustrating an eye image in FIG. 4(a).

FIGS. 5(a) and 5(b) are views illustrating a principle of the gaze point detecting process by the controller in FIG. 1, and FIG. 5(a) is a view illustrating a positional relationship between an eye ball of the object person and the imaging surface, and FIG. 5(b) is a view illustrating an eye image in FIG. 5(a).

FIG. 9(a) is a view illustrating a cursor displayed by the LCD in FIG. 1 and FIG. 9(b) is a view illustrating the image of the eye image captured by the CCD in FIG. 1.

FIG. 10(a) is a view illustrating the cursor displayed by the LCD in FIG. 1 and FIG. 10(b) is a view illustrating the image of the eye image captured by the CCD in FIG. 1.

FIG. 11(a) is a view illustrating the cursor displayed by the LCD in FIG. 1 and FIG. 11(b) is a view illustrating the image of the eye image captured by the CCD in FIG. 1.

FIG. 12(a) is a view illustrating the cursor displayed by the LCD in FIG. 1 and FIG. 12(b) is a view illustrating the image of the eye image captured by the CCD in FIG. 1.

FIG. 15(a) is a view illustrating the cursor displayed by the LCD in the variation of the present invention, and FIG. 15(b) is a view illustrating the image of the eye image captured by the CCD in the variation of the present invention.

FIG. 16(a) is a view illustrating the cursor displayed by the LCD in the variation of the present invention, and FIG. 16(b) is a view illustrating the image of the eye image captured by the CCD in the variation of the present invention.

Figure 1:
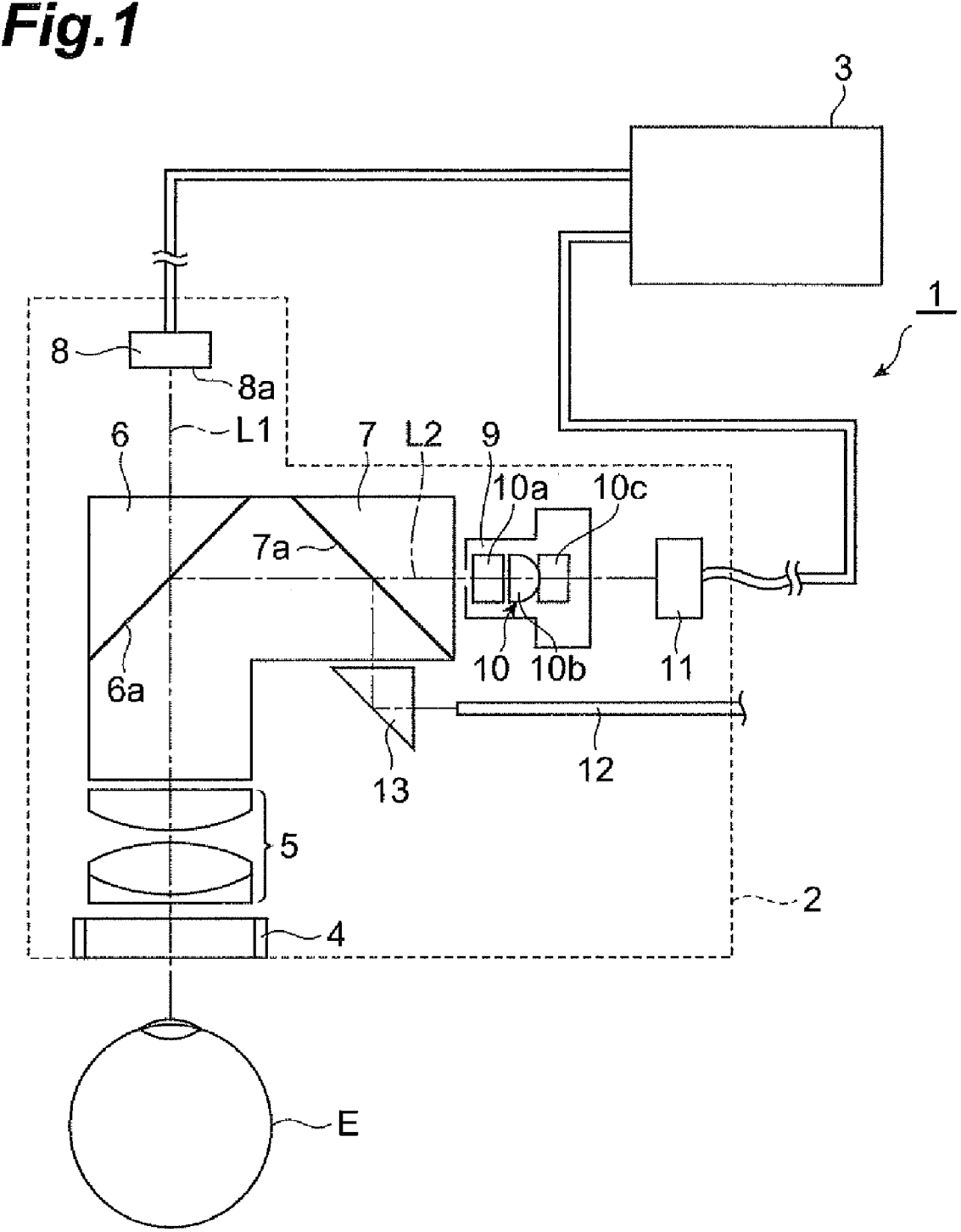
FIG. 1 is a portion of a cross sectional configuration diagram illustrating a schematic configuration of a gaze point detecting device 1 of one preferred embodiment of the present invention.

DESCRIPTION OF THE REFERENCE NUMERALS 1 gaze point detecting device
2, 102 HMD
3. controller (detecting means)
4. finder (window)
5, 105a, 105b optical system (telecentric lens)
8 LCD (image displaying means)
8a display surface
9 diaphragm (telecentric diaphragm)
11 CCD (imaging means)

BEST MODES FOR CARRYING OUT THE INVENTION

A preferred embodiment of a gaze point detecting device of the present invention will be described in detail below with reference to the accompanying drawings. In the description of the drawings, portions that are the same or equivalent are denoted by the same numerals, and duplicated descriptions thereof will be omitted. Each drawing is prepared for illustration and is shown so as to particularly emphasize object portions for illustration. For that reason, the dimension ratio of each member in the drawings does not necessary correspond to the actual ratio.

FIG. 1 is a portion of a cross sectional configuration diagram illustrating a schematic configuration of gaze point detecting device 1 of one preferred embodiment of the present invention. As illustrated in FIG. 1, the gaze point detecting device 1 includes a head mount display 2 (hereinafter, called an HMD) mounted on the head of a object person for detecting a line of sight, a personal computer connected to the HMD 2, and a controller (detecting means) 3 such as a server device. The HMD 2 actually has a case, but it is omitted in the illustration.

The HMD 2 includes a finder (window) 4 positioned in front of the eye ball E of the object person under the state that the HMD 2 is mounted on the head of the object person, an optical system (telecentric lens) 5 formed with three lenses provided inside the finder 4, a prism 6 and an LCD (image displaying means) 8 provided in this order in a direction away from the optical system 5 along an optical axis L1 of the optical system 5, a prism 7, a diaphragm (telecentric diaphragm) 9, an optical system 10, and a CCD (imaging means) 11 provided in this order in a direction away from the optical system 5 along an optical axis L2 that intersects vertically the optical axis L1 of the optical system 5, and an optical fiber cable 12 provided in parallel to the CCD 11, which are accommodated in the case of the HMD 2. Each component of the HMD 2 will be described in detail below.

The optical system 5 is a so-called telecentric lens configured so that the optical axis thereof and the principal light ray of the eye ball E side are parallel with each other. An inclined surface 6a in the optical system 5 side of the prism 6 provided on the optical axis L1 of the optical system 5 is applied with dichroic mirror coating, and transmits a display image with components of visual light projected from the display surface 8a of the LCD 8 to the optical system 5 side. On the other hand, the inclined surface 6a reflects illumination light with components of a near-infrared light emitted from the optical fiber cable 12 and entered in the inclined surface 6a along the optical axis L2 crossing vertically the optical axis L1 to the optical system 5 side and reflecting light (eye image) entered therein by reflecting the illumination light in the eye ball E, to the prism 7 side.

The prism 7 is positioned on the optical axis L2 of the optical system 5 bent by this prism 6. The inclined surface 7a of the prism 7 at the prism 6 side to which half-mirror coating is applied, transmits the eye image entered therein along the optical axis L2 to the CCD 11 side. On the other hand, the inclined surface 7a reflects the illumination light, which passes from a light source (not shown) through the optical fiber cable 12 to be irradiated, and then reflected in the prism 13 to enter therein, to the prism 6 side along the optical axis L2.

This configuration provides an optical path (a first optical path) of an image displaying optical system along the optical axis L1 and an optical path (a second optical path) of an imaging optical system along the optical axis L2, between the eye ball E and the HMD 2.

Figure 2:
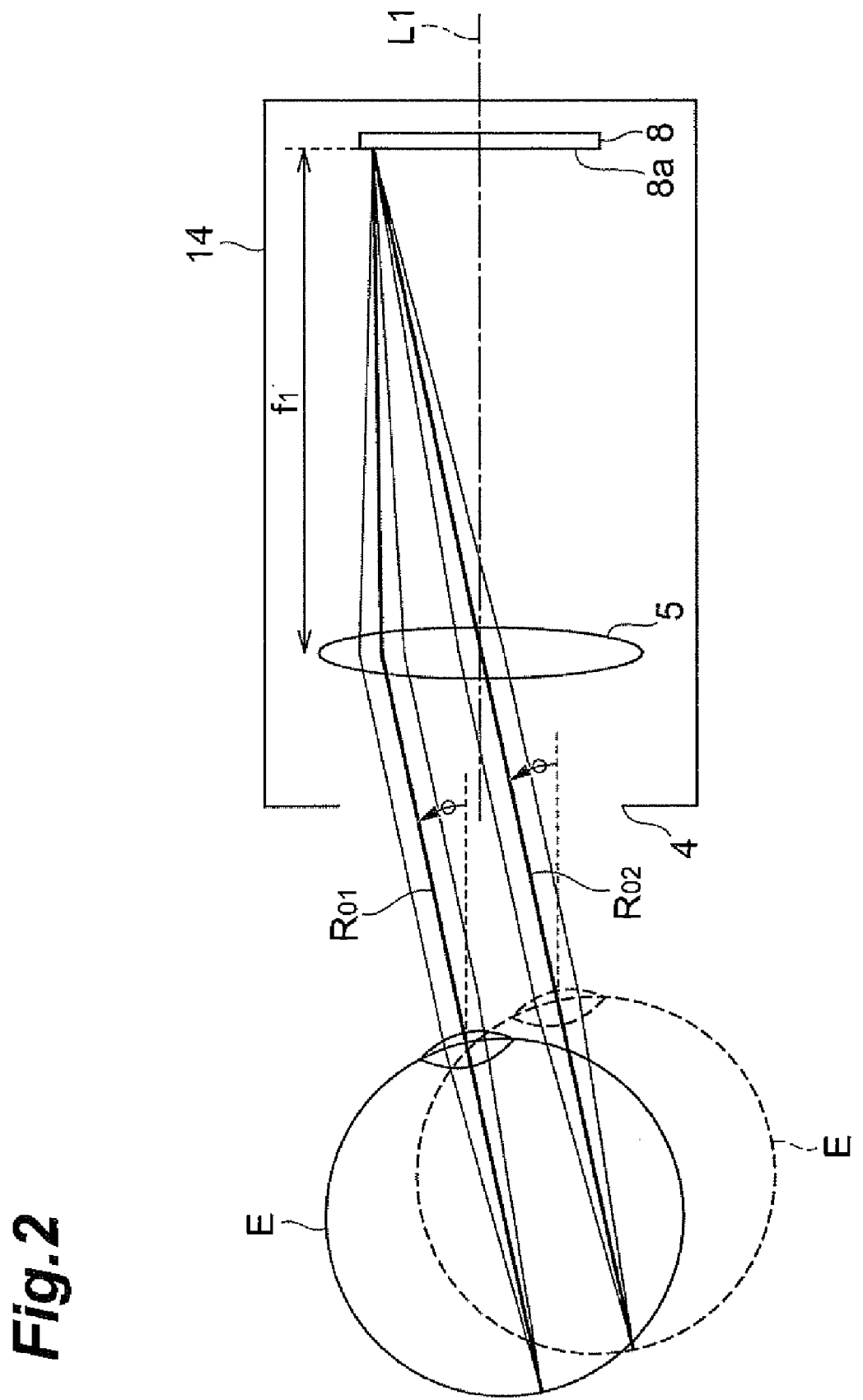
FIG. 2 is a view equivalently illustrating an optical path of an image displaying optical system in an HMD in FIG. 1.

FIG. 2 is a view equivalently illustrating the optical path of the image displaying optical system. In addition, FIG. 2 equivalently illustrates the optical system 5 as one lens. As shown in FIG. 2, the LCD 8 is placed so as to pass the optical axis L1 between the center of a display surface 8a thereof and the center of a finder 4, and is arranged so that the display surface 8a is spaced a focal length $f_1$ from the optical system 5. With this arrangement, the display image displayed on the display surface 8a of LCD 8 is output toward the optical system 5 as visible light, converted to substantially parallel light rays in the optical system 5 and the rays are projected to the external eye ball E via the finder 4. The light rays entering in the eye ball are projected onto the retina through the pupil and recognized by the object person.

Here, assuming a case in which the eye ball E deviates from the position of the solid line to the position of the dotted line, the operation of the optical system 5 causes respective principal light rays $R_{01}$, $R_{02}$ of visible light rays emitted from one point on the display surface 8a to be converted so that respective angles formed with the optical axis L1 are equal when the principal light rays are entered in the eye ball of the object person. As a result, since the principal light rays $R_{01}$, $R_{02}$, assuming that the object person has watched a same angle, are projected to a same point on the retina of the eye ball E, the display images on the display surface 8a are recognized as the images at the same position even if the relative position between the case 14 of the HMD 2 and the eye ball E deviates. For example, even if the case 14 shifts in parallel to the eye ball E when the object person watches the display image, the display image appears to be at rest. This means that, when the object person visually fixes on one point on the display surface 8a, a line of sight direction is still at rest even if the case 14 shifts. In contrast, when the case 14 rotatably moves relative to the eye ball E, the image projected from one point on the display surface 8a follows the case 14 to rotate.

Figure 3:
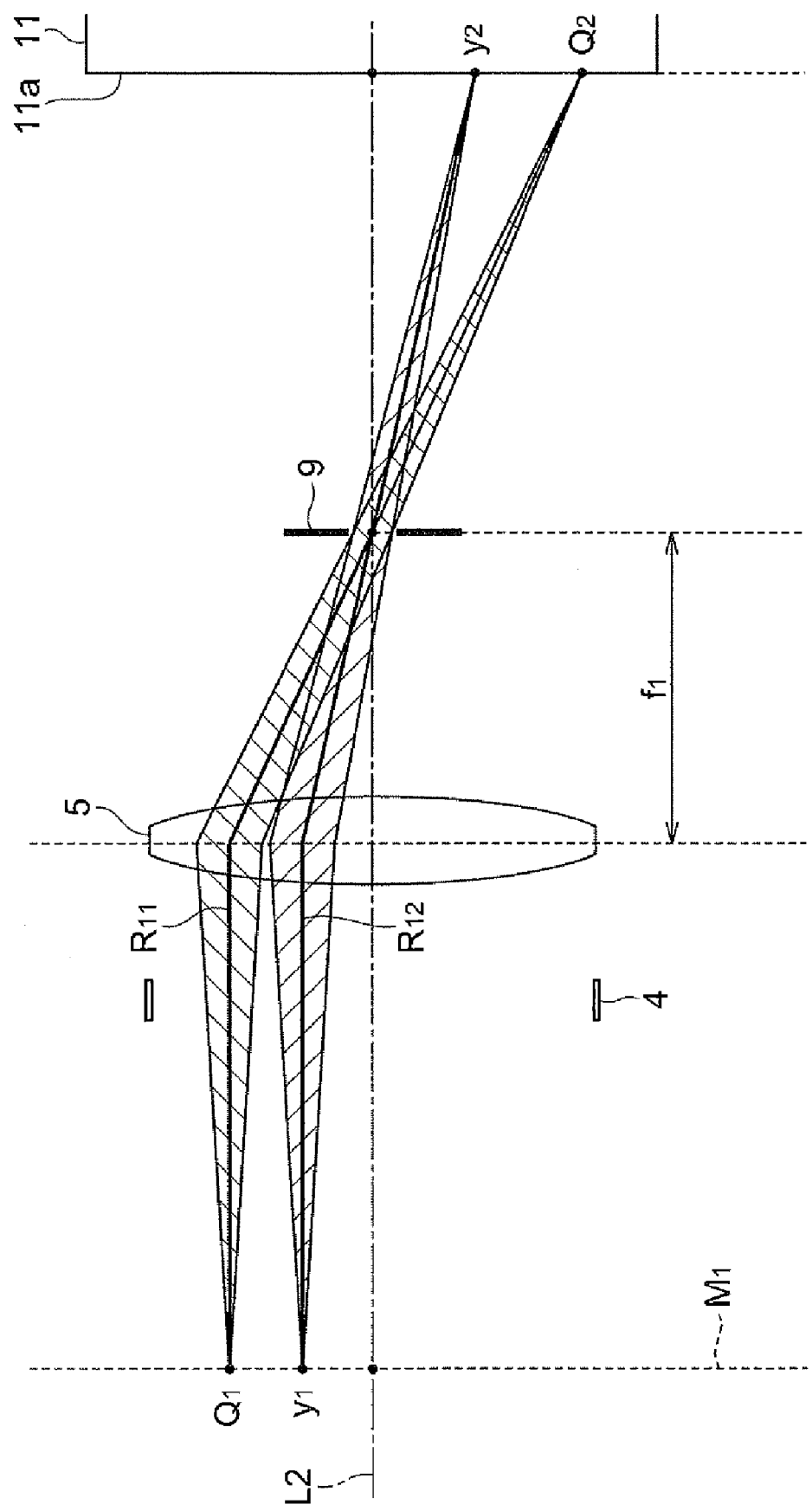
FIG. 3 is a view equivalently illustrating an optical path of an imaging optical system in the HMD in FIG. 1.

FIG. 3 is a view equivalently illustrating the optical path of the imaging optical system. In addition, FIG. 3 equivalently illustrates the optical system 5 as one lens. As illustrated in FIG. 3, the optical system 5 is arranged on the optical axis L2 between the finder 4 and the CCD 11, and the diaphragm 9 is arranged spaced a focal length $f_1$ from the optical system 5 so that the optical axis L1 passes through the center of the diaphragm 9. The diaphragm 9 is set to a proper internal diameter so that the image captured by CCD 11 does not darken.

The optical system 5 and the diaphragm 9 constitute a telecentric optical system. Specifically, the light rays emitted from a point $Q_1$ on a surface $M_1$ positioned in the opposite side of the diaphragm 9 of the optical system 5 is narrowed down to a diagonal portion by the diaphragm 9 and forms an image at a point $Q_2$ on the imaging surface 11a of the CCD 11, and the light rays emitted from a point $y_1$ on the surface $M_1$ is narrowed down to a diagonal portion and forms an image at a point $y_2$ on the imaging surface 11a. As a result, respective light rays including the principal light rays $R_{11}$ and $R_{12}$ are limited, when the light rays enter the optical system 5, to substantially parallel light rays to the optical axis L2 and enter the imaging surface 11a. Thus, even if the distance between the optical system 5 and an object varies, the size of the image captured by the CCD 11 does not change.

Considering the surface $M_1$ as the surface of the eye ball in such an imaging optical system, the image (eye image) created by the light rays reflected from the object person in response to the illumination light irradiated from the optical fiber cable 12 to the outside through the finder 4 is captured by the imaging surface 11a of the CCD 11 through the optical system 5 and the diaphragm 9. At this point, the distance between the CCD 11, the light source, and the eye ball of the object can be considered to be infinite.

In other words, the optical system 5 constituting a portion of the telecentric optical system of the imaging optical system is shared with an optical system of the image displaying optical system.

Referring back to FIG. 1, an optical system 10 arranged on the optical axis L2 between the diaphragm 9 and the CCD 1 includes a visible light shielding filter (infrared transmission filter) 10a and lenses 10b and 10c and is provided to cut off components of visible light entered to the imaging surface 11a and to correct aberration.

A controller 3 is a computer system includes CPU, a memory, and an input-output device, for producing image signal to display on an LCD 8 and receives image data captured by the CCD 11 to perform an image process. Also, the controller 3 conducts a gaze point detecting process for detecting a gaze point on the display surface 8a of the object person, and a gaze point calibrating process for correcting the gaze point detected. Each process that is to be conducted by the controller 3 is described below.

(Gaze Point Detecting Process)

First, the principle of the gaze point detecting process conducted by the controller 3 is described with reference to FIGS. 4 and 5.

Generally, the eye ball of the object person can approximately be modeled to a dual ball constituted of the eye ball E and the corneal-ball C (refer to FIG. 4(a)). Since the distance between the CCD 11 and the eye ball E and the distance between the light source 15 and the eye ball E are considered infinite and it can be considered that the light source 15 is present on the optical axis L2 of CCD 11, the illumination light from the light source 15 is irradiated to the eye ball E, as parallel light. When a line of sight vector $D_1$ indicating a line of sight direction of the object person faces the direction along the optical axis L2, the optical path of light reflected (corneal reflection) in the surface of the corneal-ball C in response to the illumination light is nearly coincident with the optical path of the light reflected from the center $C_p$ of the pupil. Accordingly, the position $P_{01}$ of the corneal reflection captured by the imaging surface 11a is nearly coincident with the position $P_{02}$ of the center of the pupil (refer to FIG. 4(b)). Even if the eye ball E is positioned at any portion of the captured eye image $G_{01}$ at this time, it can be considered that the eye ball E is constantly located at an infinite distance from the imaging surface 11a. Thus, the positional relationship between the position $P_{01}$ of the corneal reflection and the position $P_{02}$ of the center of the pupil does not change.

In contrast, when a line of sight vector $D_2$ of the object person faces the diagonal direction shifted from the optical axis L2, the shift in coordinates of the relative positional relationship between the position $P_{11}$ of the corneal reflection and the position $P_{12}$ of the center of the pupil in an eye image $G_{02}$ captured increases in proportional to the angle formed by the line of sight vector $D_2$ and the optical axis L2 (refer to FIGS. 5(a) and 5(b)). At this time, even if the eye ball E is positioned at any portion of the captured eye image $G_{02}$, the positional relationship between the position $P_{11}$ of the corneal reflection and the position $P_{12}$ of the center of the pupil does not change. In addition, even if the distance between the eye ball E and the imaging surface 11a changes by a finite value, the positional relationship does not change. Accordingly, even if the position of the eye ball E and the imaging surface 11a shifts three-dimensionally, when the positional relationship between the position of the corneal reflection and the position of pupil center that are captured is detected, the line of sight direction of the object person can be specified even if the positional relationship between the eye ball E and the CCD 11 and the relationship between the eye ball E and the light source 15 are unknown.

In order to utilize the principle above, first, the controller 3 detects the position of the corneal reflection by comparing a predetermined threshold with the brightness of the eye image, based on the eye image output from the CCD 11. Further, the controller 3 detects the central position of the pupil based on the face image of the object person including the eye image. In particular, since the face image captured by the CCD 11 has the property that the brightness of the pupil is higher than that of the peripheral of the pupil in the face due to irradiation of the light having components of near-infrared rays, the controller 3 can detect the position of the pupil by detecting this difference in brightness. Then, the controller 3 specifies the outline of the pupil detected; calculates the ellipse capable of approximating the outline; and determines the center of the ellipse as the center of the pupil.

The controller 3 may also detect the position of the pupil by alternately lighting illumination light with a wavelength of around 850 nm and illumination light with a wavelength of around 950 nm from the light source at light intensity at which the brightness on the surface of the face of the object person is the same and then acquiring differences in the face image obtained. In this manner, the level of the reflection light of the portion of the pupil with the wavelength of 850 nm is higher than that of the reflection light with the wavelength of 950 nm and portions except the pupil are counterbalanced by taking differences. Thus, the portion of the pupil can be detected more precisely.

The controller 3 detects the gaze point of the object person in the following manner, based on the position of the corneal reflection and the position of pupil center obtained as described above.

Figure 6:
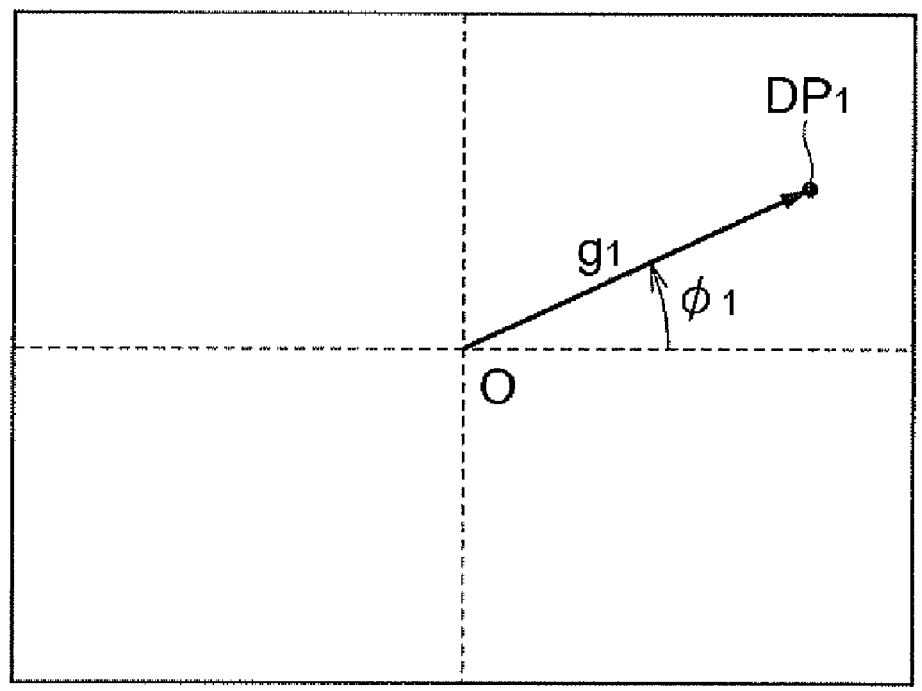
FIG. 6 is a view illustrating an image of a display image displayed by an LCD in FIG. 1.
Figure 7:
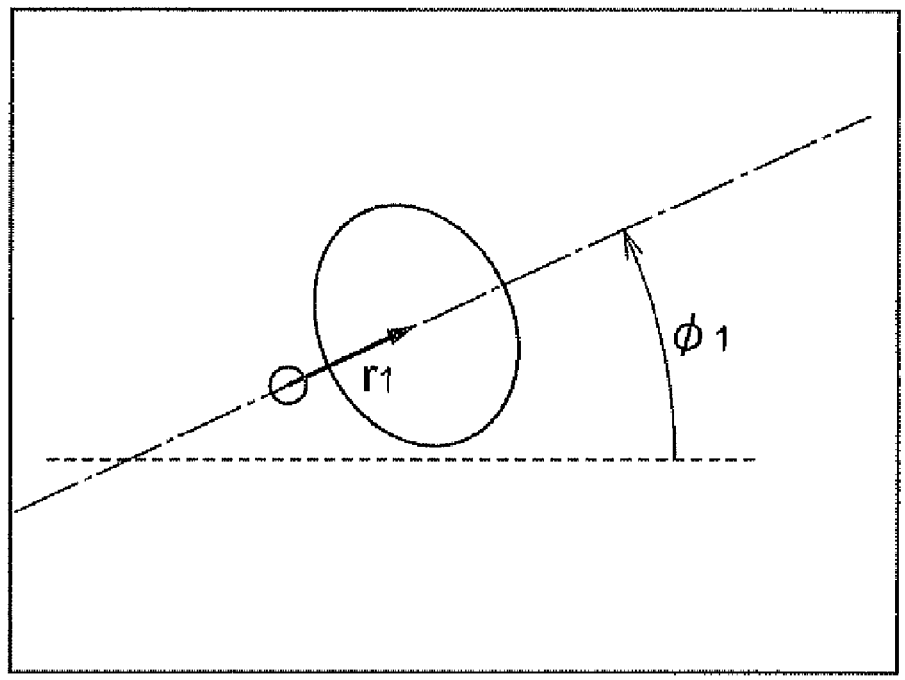
FIG. 7 is a view illustrating an image of the eye image captured by a CCD in FIG. 1.

The case that the display image illustrated in FIG. 6 is displayed by the LCD 8 is considered. Here, it is assumed that the object person watches a point $DP_1$ spaced by position vector $g_1$ apart from the origin O positioned at the center of the display surface 8$a$. In this case, the eye image as illustrated in FIG. 7 is captured by the CCD 11, and the controller 3 calculates the vector $r_1$ from the position of corneal reflection to the position of pupil center, as the relative positional relationship. The center O of the display surface 8$a$ of the LCD 8 is coincident with the optical axis L2 passing the center of the imaging surface 11$a$ and the optical path of the light source, from a point of view of the object person. Thus, watching the center O is equal to watching the center of the imaging surface 11$a$. In addition, as previously stated, when the object person watches the center of the imaging surface 11$a$, the image positions of the corneal reflection and the center of the pupil are coincident. Accordingly, the angle formed by the horizontal axis of the display surface 8$a$ and the position vector $g_1$, and the angle formed by the horizontal axis of the imaging surface 11$a$ and the vector $r_1$ are coincident at $\phi_1$.

Using the proportional relationship between the magnitude $|g_1|$ of the position vector $g_1$ and the magnitude $|r_1|$ of the vector $r_1$, the controller 3 calculates the position vector $g_1$ from a proportionality coefficient previously determined and then detects the gaze point $DP_1$ on the display surface 8$a$.

(Gaze Point Calibrating Process)

Figure 8:
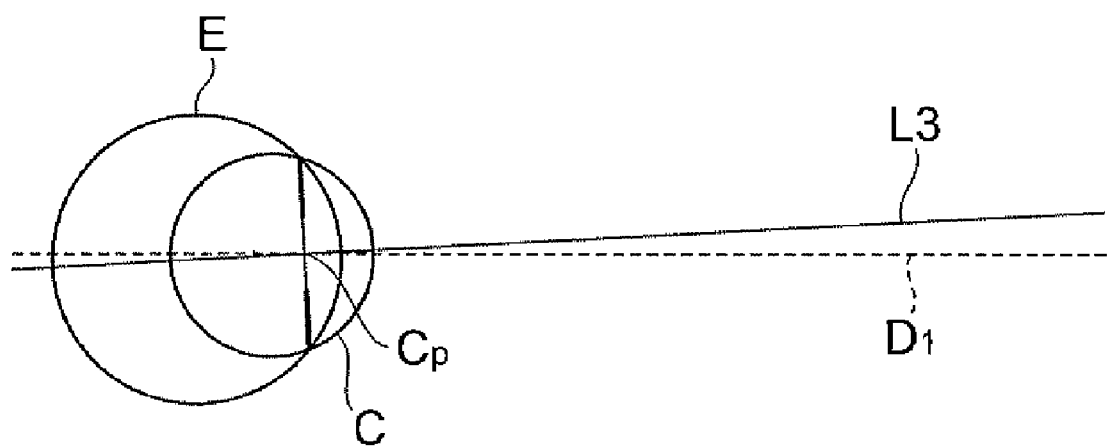
FIG. 8 is a view illustrating relation between an optical axis of the eye ball and a sighting axis of the object person.

However, in an actual human eye ball E, a direction of the optical axis L3 of the eye ball E is different from a sighting axis $D_1$ indicating the line of sight direction, as illustrated in FIG. 8. The optical axis L3 described here is considered a straight line passing the center of the eye ball E and the center $C_p$ of the pupil, and is a symmetric axis of the eye ball optical system. Also, the sighting axis $D_1$ is an axis indicating an optical path when an image is projected to a central fovea that is the highest portion in resolution of eyesight on the retina. Generally, it is considered that a view-object is present at the end of the sighting axis. In this manner, when the display image as illustrated in FIG. 9($a$) is displayed on the LCD 8 and a view-object is positioned at the origin O, the position $P_{21}$ of the corneal reflection and the position $P_{22}$ of the center of the pupil on the imaging surface 11$a$ are misaligned as illustrated in FIG. 9($b$). For this amount of misalignment, there is an individual variation for each object person, and thus, the relation between the magnitude $|g_1|$ of the position vector $g_1$ (refer to FIG. 6) and the magnitude $|r_1|$ of the vector $r_1$ (refer to FIG. 7) is not uniformly determined. Therefore, the controller 3 performs a gaze point calibrating process in the following manner.

First, the controller 3 moves, while displaying a cursor (index image) $Cu_1$ on the display surface 8$a$, the cursor $Cu_1$ in the direction that the position $P_{31}$ of the corneal reflection and the position $P_{32}$ of the center of the pupil are coincident in the captured eye image, and searches the coordinates of the cursor (first index image) $Cu_1$ at which both the positions $P_{31}$, $P_{32}$ are coincident to store it (refer to FIGS. 10($a$) and 10($b$)). Consequently, the point stored is replaced as a new origin O' (refer to FIG. 11($a$)).

After such origin correction, as illustrated in FIG. 12($a$), the controller 3 calculates a vector $r_2$ from the position of the corneal reflection to the position of the center of pupil in the eye image illustrated in FIG. 12($b$) upon displaying a cursor (second index image) $Cu_2$ at another position on the display surface 8$a$. Then, the controller 3 determines the position vector $g_2$ of the cursor $Cu_2$ origin-corrected for the position of the cursor $Cu_1$ and the coefficient k indicating the relation with the vector $r_2$ based on the following formula (1);

$$|g_2|=k|r_2| \qquad (1)$$

Also, when the case of the HMD 2 is mounted diagonally relative to the eye ball, the angle $\phi_2'$ formed by the horizontal axis of the display surface 8$a$ and the position vector $g_2$, and the angle $\phi_2$ formed by the horizontal axis of the imaging surface 11$a$ and the vector $r_2$ have different values respectively. Then, the controller 3 determines an angle correction value $\Delta\phi$ by the following formula (2);

$$\phi_2-\phi_2'=\Delta\phi \qquad (2)$$

Next, the controller 3 determines a vector $r_3$ from the position of corneal reflection to the position of pupil center when an actual gaze point is detected, and thereafter, the angle $\phi_3$ formed by the horizontal axis of the imaging surface 11$a$ and the vector $r_3$ is corrected by $\Delta\phi$ using the following formula (3);

$$\phi_3'=\phi_3-\Delta\phi \qquad (3)$$

Thereby, the controller 3 determines the angle $\phi_3'$ formed by the horizontal axis of the imaging surface 8$a$ and the position vector $g_3$ of a gaze point detection object.

Finally, the controller 3 calculates the gaze point coordinate $g_3(x,y)$ of the object person to the origin O' ($x_0'$, $y_0'$) by the following formula (4);

$$(x,y)=(x0'+k|r_3|\cos\phi_3', y0'+k|r_3|\sin\phi_3') \qquad (4)$$

In addition, when the visual angle of the object person to the display surface 8$a$ of LCD 8 is small, the linear relationship between the position vector $g_2$ and the vector $r_2$ is held. However, when the visual angle is large, the relation between both vectors is determined in the following manner. Namely, the controller 3 displays a plurality of cursors $C_u$ on the display surface 8$a$, and stores both vectors $g_2$, $r_2$ when the object person watches the cursor. Then, the controller 3 performs curve fitting (curve approximation) and determines the coefficients a, b, using the following formula (5);

$$|g_2|=a|r_2|^b \qquad (5)$$

Also, the controller 3 determines an angle correction value $\Delta\phi$ for each cursor Cu using the formula (2), and calculates an angle formed by the position vector $g_3$ by applying the mean value to the formula (3).

Figure 13:
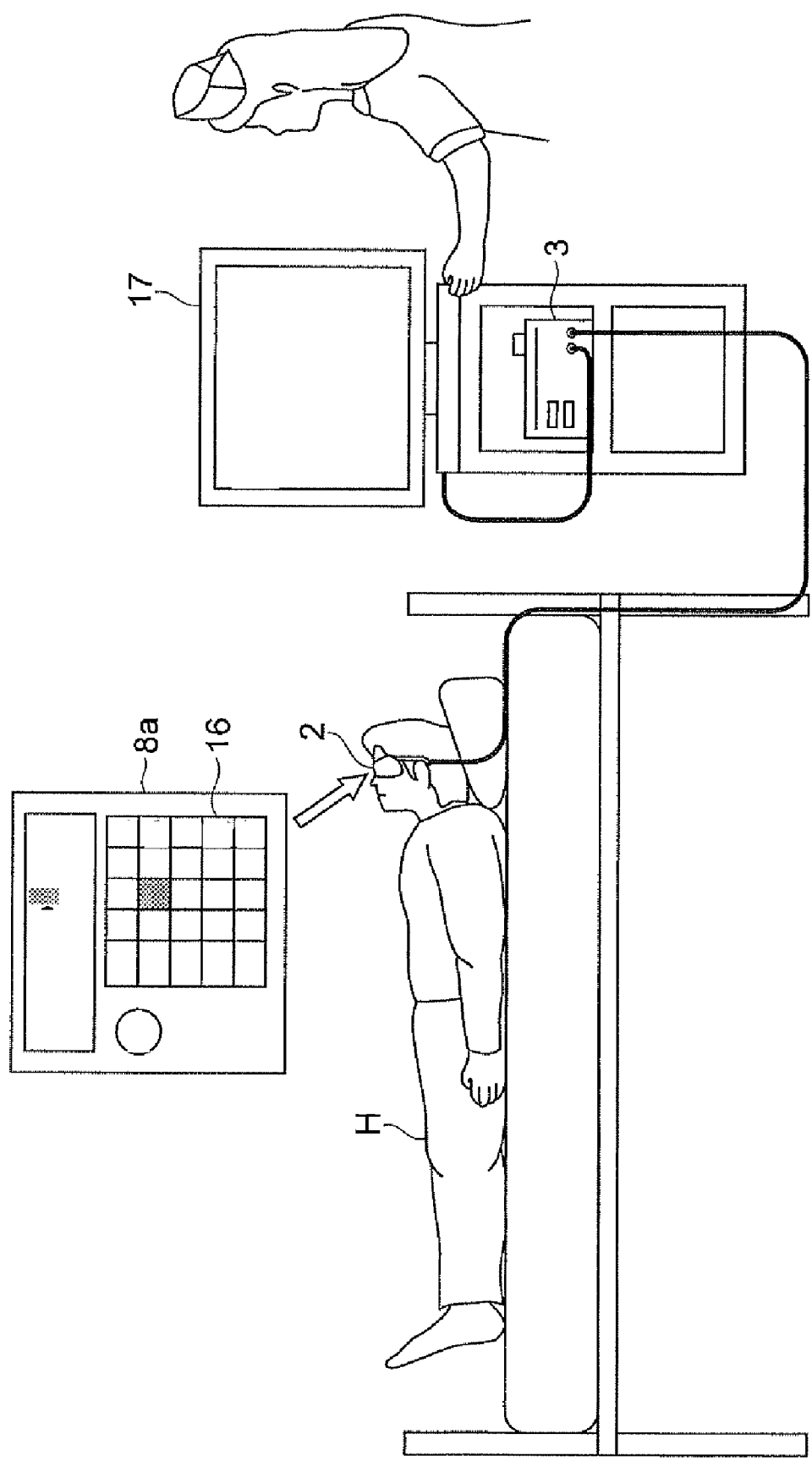
FIG. 13 is a conceptual diagram illustrating an application example of the gaze point detecting device of the present invention.

The application example of the gaze point detecting device 1 described above will be described. FIG. 13 is a conceptual diagram illustrating the application example of the gaze point detecting device 1. As illustrated in FIG. 13, the HMD 2 is mounted to the eye of an object person H of interest, such as a patient, via glasses, and a personal computer (detecting means, input character specifying means) 3 connected to the outside of HMD 2 displays a selection image 16 that is divided to a plurality of ranges for selecting input characters, on the display surface 8a. When the position of the gaze point on the selection image 16 of the object person H is detected and then the position of the gaze point is recognized in a specified range for a predetermined hours or greater, when the blink of the object person H is detected in a specified range, or when operation, such as a button (not shown), by a portion of a hand or a foot of the object person (e.g., only a big toe) is detected, if the portion has a remaining function, the personal computer 3 specifies as an input character corresponding to a range thereof that is input by the person H. In addition, the personal computer 3 outputs, when an input character is recognized, the character to a display (information displaying unit) 17 connected to the outside upon voice-outputting the character. Thus, even if a disabled person, such as a patient, is set as an object person, nearby individuals can easily read the will of the object person.

In such a gaze point detecting device 1, when a display image is projected from a finder 4 to the outside, it passes the optical system 5 that is spaced a focal length $f_1$ from the display surface 8a, thereby one point on the display surface 8a corresponds to an angle of the line of sight of the object person on a one-to-one basis. At the time, the eye image of the object person is displayed on the CCD 11 through the telecentric optical system in response to irradiation of the illumination light, and thereby the size of the captured eye image does not change even if the position of the object person changes in the front/back direction to the finder 4. In other words, since the object person is imaged from infinity while being irradiated by light form infinity, the relative relationship between the center of the pupil and the position of the corneal reflection does not change as long as the line of sight of the object person faces a definite direction even if the shift between the case of HMD 2 and the eye ball occurs. With this arrangement, when the gaze point is detected based on the eye image of the object person, an actual gaze point of the object person on the display surface 8a and the line of sight direction detected correspond on a one-to-one basis. Thus, an error in the gaze point detection of the object person is reduced even if the position of the object person relative to the case changes.

Particularly, since the controller 3 calculates the gaze point position in response to the positional relationship between the position of the corneal reflection and the position of pupil center in the eye image, the positional relationship between the position of the corneal reflection and the position of pupil center in the eye image detected does not change even if the position of the object person changes to the window in the vertical direction or the horizontal direction. Thus, an error in the gaze point detection of the object person is surely reduced.

Also, a gaze point calibrating process is performed in the controller 3, and thereby an error in the gaze point detection of the object person is further reduced by determining the positional relationship between the position of corneal reflection and the position of pupil center to a previously displayed cursor and calibrating the gaze point position, even when the optical axis of the eye ball and the direction of the line of sight (sighting axis) of the object person are different.

Figure 14:
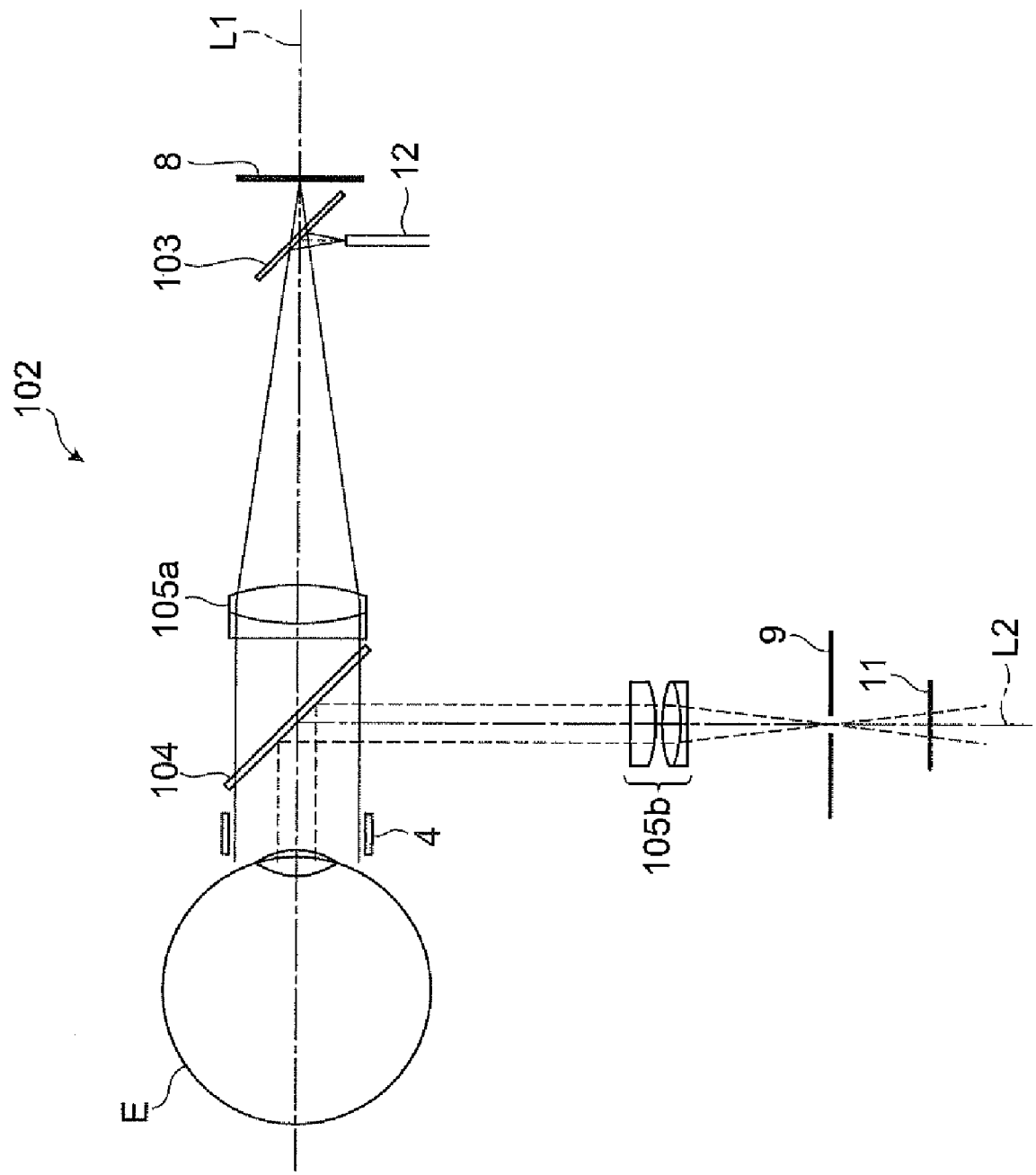
FIG. 14 is a view illustrating a schematic configuration of an HMD of a variation of the present invention.

In addition, the invention is not limited to the embodiment described above. For example, for the arrangement of each component of the HMD 2 on the optical axes L1, L2, various modifications can be employed. For example, similarly to an HMD 102 of a variation of the present invention illustrated in FIG. 14, an optical system 105a of a telecentric lens provided on the optical axis L1 of the image displaying optical system and an optical system 105b of a telecentric lens 105b provided on the optical axis L2 of the imaging system are separately placed. Also, as illustrated in FIG. 14, it may be configured so that illumination light irradiated from the optical fiber cable 12 is irradiated along the optical axis L1 of the image displaying optical system. In addition, this illumination light may be irradiated from a small light source device, such as an LED, fixed to a position corresponding to the top end of the optical fiber cable 12 in FIG. 14. In such an HMD 102, a dichroic mirror 103 is arranged on the front surface of LCD 8 that reflects the illumination light in the direction along the optical axis L1 and transmits the display image displayed by the LCD 8 along the optical axis L1, and a half-mirror 104 is arranged inside the finder 4 that reflects light that is reflected from the eye ball of the object person by the illumination light, in the direction along the optical axis L2.

Also, the controller 3 may process in the manner below, as a substitute for the gaze point calibrating process described above. Specifically, the controller 3 displays a cursor $Cu_3$ at the origin O on the display surface 8a as illustrated in FIG. 15(a), and calculates a vector $\Delta r$ (refer to FIG. 15(b)) from the position of the corneal reflection at that time to the position of pupil center. Then, the controller 3 displays another cursor $Cu_4$ (refer to FIG. 16(a)) at another position different from that of the cursor $Cu_3$ and determines a vector $r_4$ (refer to FIG. 16(b)) from the position of the corneal reflection at that time to the position of pupil center. Then, the controller 3 corrects the vector $r_4$ to the vector $r_4'$ using the following formula (6);

$$r_4' = r_4 - \Delta r \qquad (6)$$

As described above, thereafter, the controller 3 applies the vector $r_4'$ to the formulas (1) and (2) and therewith corrects the vector from the position of the corneal when the gaze point is detected to the position of pupil center using the formula (6) above. After the correction, the controller 3 can detect the gaze point on the display surface 8a by applying the formulas (3) and (4). With such the gaze point calibrating process, the object person has no need to track the sight of the cursor, and thus, the position of the gaze point can be detected with high precision, without placing a load to a user.

Also, the controller 3 is not limited to a device externally connected to the HMD 2, but may be an arithmetic device such as CPU board built in the case of HMD 2.

It is preferable that the present invention has further a telecentric diaphragm arranged at the focal position of the telecentric lens on the optical path between the window and the imaging means.

In addition, it is preferable that the displaying surface of the image displaying means is arranged at the focal position of the lens arranged between the image displaying means and the window.

Also, it is preferable that the illumination light is irradiated from a light source that is considered to be positioned at an infinite distance from the object person on the optical path between the image displaying means and the window. In this manner, even when the position of the object person shifts, the illumination light to be irradiated is constantly irradiated as parallel light, and thus, the line of sight direction of the object person is stably detected.

It is also preferable that the detecting means detects the position of the corneal reflection and the position of pupil center in the eye image and calculates the position of the gaze point according to a positional relationship between the position of the corneal reflection and the position of pupil center. In this case, the positional relationship between the position of the corneal reflection and the position of pupil center in the eye image detected does not change even if the position of the object person changes to the window in the vertical direction or the parallel direction. Thus, an error in the gaze point detection of the object person is surely reduced.

It is also preferable that the detecting means detects, while displaying an index image on the image displaying means, the position of the corneal reflection and the position of pupil center and searches for a coordinate of the first index image at which the position of the corneal reflection coincides with that of the pupil center, and also the detecting means determines, while displaying a second index image at a position different from that of the first index image on the image displaying means, a positional relationship between the position of corneal reflection and the position of pupil center and then, calibrates the position of gaze point based on the positional relationship and the coordinates of the first and the second index images. Thus, an error in the gaze point detection of the object person is further reduced by previously determining the positional relationship between the position of corneal reflection and the position of pupil center to the index image and calibrating the gaze point position, even when the optical axis of the eye ball and the direction of the line of sight (sighting axis) of the object person are different.

Further, it is preferable that the detecting means determines, while displaying a first index image at a specified position on the image displaying means, a first positional relationship between the position of corneal reflection and the position of pupil center, and the detecting means determines, while displaying a second index image at a position different from that of the first index image in the image displaying means, the second positional relationship between the position of the corneal reflection and the position of pupil center and then calibrates the position of gaze point based on the first and second positional relationship and the coordinates of first and second index images. With this configuration, an error in the gaze point detection of the object person is further reduced by previously determining the positional relationship between the position of corneal reflection and the position of pupil center to the index image and calibrating the gaze point position, even when the optical axis of the eye ball and the direction of the line of sight (sighting axis) of the object person are different.

It is also preferable to further include an input character specifying means for specifying, after making the image displaying means display a selection image that makes the object person select input characters, the input characters based on a position of gaze point detected by the detecting unit. Thus, even if the position of the object person changes when the object person inputs characters by only the movement of the line of sight, precision in inputting characters and user's convenience can be improved.

Further, it is preferable that the input-character specifying means also outputs the specified input characters to an external information displaying means. With this configuration, since input characters input by the object person can be read, and thereby it is possible to grasp the will of the object person.

INDUSTRIAL APPLICABILITY

The present invention aims at use for a line of sight detecting device that detects the gaze point of the object person relative to the image displayed, and improves the precision in the gaze point detection of the object person to the display image, while maintaining the convenience for a user.

The invention claimed is:

1. A gaze point detecting device for detecting a gaze point in a display image of an object person by projecting a display image displayed by an image displaying means to outside via a window and capturing an eye image of the object person through an imaging means, in response to an illumination light irradiated toward the object person positioned outside of the window, the device comprising:
    a telecentric lens arranged on an optical path between the window and the imaging means, for limiting the eye image to light parallel to the optical path and entering the light in the imaging means; a telecentric diaphragm arranged at a focal position of the telecentric lens;
    a lens arranged on an optical path between the image displaying means and the window, for constituting a part of the telecentric lens; and
    a detecting means for detecting a position of the gaze point of the object person based on the eye image captured by the imaging means,
    wherein a display surface of the image displaying means is arranged at the focal position of the lens arranged between the image displaying means and the window, and thereby a display image from a predetermined position of the image displaying means is converted to parallel light to be projected to the outside.

2. The gaze point detecting device according to claim 1, wherein the illumination light is irradiated from a light source that is considered to be located at an infinite distance from the object person on the optical path between the image displaying means and the window.

3. The gaze point detecting device according to claim 1, wherein the detecting means detects a position of corneal reflection and a position of pupil center in the eye image and calculates the position of gaze point according to a positional relationship between the position of corneal reflection and the position of pupil center.

4. The gaze point detecting device according to claim 3, wherein the detecting means detects, while displaying an index image on the image displaying means, the position of corneal reflection and the position of pupil center and searches for a coordinate of a first index image at which the position of corneal reflection coincides with that of the pupil center, and also the detecting means determines, while displaying a second index image at a position different from that of the first index image on the image displaying means, a positional relationship between the position of corneal reflection and the position of pupil center, and then calibrates the position of gaze point based on the positional relationship and the coordinates of first and second index images.

5. The gaze point detecting device according to claim 3, wherein the detecting means determines, while displaying a first index image at a specified position on the image displaying means, a first positional relationship between the position of corneal reflection and the position of pupil center, and the detecting means determines, while displaying a second index image at a position different from that of the first index image in the image displaying means, a second positional relationship between the position of corneal reflection and the position of pupil center and then calibrates the position of gaze point based on the first and second positional relationships and the coordinates of first and second index images.

6. The gaze point detecting device according to claim 1, further comprising: an input character specifying means for specifying, after making the image displaying means display a selection image that allows the object person to select input characters, the input characters based on a position of gaze point detected by the detecting means.

7. The gaze point detecting device according to claim 6, wherein the input character specifying means outputs the specified input characters to an external information displaying means.

* * * * *